(12) United States Patent
Suzuki

(10) Patent No.: US 6,508,843 B2
(45) Date of Patent: Jan. 21, 2003

(54) KNEE JOINT STRUCTURE OF ARTIFICIAL LIMB

(75) Inventor: Mitsuhisa Suzuki, Aichi (JP)

(73) Assignee: Imasen Engineering Corporation, Inuyama Aichi (JP)

( * ) Notice: Subject to any disclaimer, the term of this patent is extended or adjusted under 35 U.S.C. 154(b) by 0 days.

(21) Appl. No.: 09/933,830

(22) Filed: Aug. 22, 2001

(65) Prior Publication Data

US 2002/0026246 A1 Feb. 28, 2002

(30) Foreign Application Priority Data

Aug. 22, 2000  (JP) ........................................ 2000-250461

(51) Int. Cl.[7] ................................ A61F 2/68; A61F 2/64
(52) U.S. Cl. ............................................. 623/46; 623/44
(58) Field of Search ............................. 623/39, 43, 44, 623/46

(56) References Cited

U.S. PATENT DOCUMENTS

| | | | |
|---|---|---|---|
| 4,215,442 A | * | 8/1980 | Blatchford et al. ............ 623/44 |
| 5,181,931 A | * | 1/1993 | Van de Veen .................. 623/40 |
| 5,201,776 A | * | 4/1993 | Freeman ........................ 623/46 |
| 5,545,232 A | * | 8/1996 | Van de Veen .................. 623/39 |
| 5,728,173 A | * | 3/1998 | Chen ............................. 623/44 |
| 6,086,616 A | * | 7/2000 | Okuda et al. .................. 623/44 |

* cited by examiner

Primary Examiner—David H. Willse
Assistant Examiner—Javier G. Blanco
(74) Attorney, Agent, or Firm—Sughrue Mion, PLLC

(57) ABSTRACT

A knee joint structure has a five-joint link structure in which there are an upper link 1 to which a thigh support part of an artificial limb 10 is fixed; a lower link 4 with which a foot part 11 of the artificial limb is linked; a rear link 5 for linking the upper and lower links 1 and 4 with each other; a main frontal link 2 linked with the frontal of the upper link 1; and an auxiliary frontal link 3 for linking the main frontal link 2 and the lower link 4 with each other. In addition, there is provided an elastic element 8 acting to increase an angle formed by the auxiliary frontal link 3 and the lower link 4.

8 Claims, 18 Drawing Sheets

KNEE JOINT STRUCTURE OF ARTIFICIAL LIMB

BACKGROUND OF THE INVENTION

1. Field of the Invention

The present invention relates to a knee joint of an artificial limb.

2. Description of the Related Art

A conventional knee joint of an artificial limb includes a single axis. Such single axis based knee joint is structurally simple, but the single axis must be set rearward of a leg in order to prevent knee from bending the moment an ankle comes into contact with a ground level, and an ankle load is applied to an artificial limb. As a result, movement of the artificial limb becomes unnatural. Thus, a knee joint structure adopting a four-joint link mechanism is often employed. In the four-joint link mechanism, a virtual center axis during an idle leg phase can be set upward of the link mechanism, thus providing excellent control properties. A description will be given by referring to the accompanying drawings.

FIG. 1 is a diagram of a knee joint employing a conventional four-joint link mechanism. The knee joint is composed of a link mechanism that comprising four links 101, 102, 103, and 104. Upper link 101 is fixed to a thigh support part 110 of an artificial limb. Lower link 103 is linked with a foot part 111 of the artificial limb. A stopper 105 for preventing angle formed by the upper link 101 and the front link 102 from extending over a predetermined angle is provided at the upper link 101. The stopper 105 stops knee stretching. During the idle leg phase, a cross point between an extension line of the front link 102 and that of the rear link 104 is defined as a virtual rotation center axis P101. In the example of FIG. 1, a link mechanism is constructed so that an initial position of the virtual rotation center axis P101 is positioned far above and at the rear of the link mechanism.

Thus, lines of action F101 and F102 of a load during ankle landing at a moment when the idle leg phase goes to a leg grounding phase, i.e., when a foot part 111 comes into contact with a ground level GL extend forward of the virtual rotation center axis P101, and never come rearward. Thus, knee is not bent during ankle landing, by which walking is stable. The line of action F101 indicates a case in which a stretched muscle of a thigh joint of a physically handicapped person wearing an artificial limb is strong, and the line of action F102 indicates a case in which the stretched muscle of the thigh joint is weak. Next, lines of action of a load when walking is advanced, and a toe leaves the ground level GL, i.e., during toe take-off are defined as F103 and F104. The line of action F103 indicates a case in which the bent muscle of the thigh joint of the physically handicapped person is strong, and the line of action F104 indicates a case in which the bent muscle of the thigh joint is weak. The line of action F103 when the bent muscle is strong passes through the rear of the virtual rotation center axis P101, and thus, knee bending takes place during toe take-off, enabling smooth walking. However, in the case where the bent muscle is weak, the line of action F104 passes through front of the virtual rotation center axis P101. Thus, knee bending cannot be done, and smooth toe take-off cannot be done.

On the other hand, as shown in FIG. 2, in a four-joint link mechanism constructed so that the virtual rotation center axis P102 is positioned to be comparatively forward, during toe take-off, the line of action F103 in the case where the bent muscle is strong and the line of action F104 in the case where the bent muscle is weak as well pass through the rear of the virtual rotation center axis P102. Thus, knee bending taken place, enabling smooth toe take-off. However, when the ankle is landed, in the case where the stretched muscle is strong, the line of action F101 passes through the sufficient front of the virtual rotation center axis P102, and thus, there is no worrying about knee bending. However, in the case where the stretched muscle is weak, the line of action F102 passes through the vicinity of the virtual rotation center line P102. Thus, knee bending sometimes takes place, and walking may become unstable.

SUMMARY OF THE INVENTION

In this way, in the knee joint using the four-joint link mechanism, the prevention of knee bending during ankle landing and smooth knee bending during toe take-off become a matter of antinomy. Thus, it has been necessary to design a moderate link mechanism between the mechanism of FIG. 1 and that of FIG. 2, which is extremely drawn, according to the muscle power of the physically handicapped person wearing the artificial limb or it has been necessary for the physically handicapped person to master how to use the stretched muscle during ankle landing or how to use the bent muscle during toe take-off according to the characteristics of the link mechanism of the provided artificial limb through training.

In order to mitigate the above described matter of antinomy, U.S. Pat. No. 5,181,931 proposes that a length of one link of the four-joint links is contracted due to a load. However, this apparatus requires a sliding portion for contracting and extending the length of the link, and a mechanism becomes more complicated as compared with a pure link mechanism in which a movable part is formed of an axis that is a joint. Thus, there has been a problem in view of cost efficiency or durability.

Accordingly, it is an object of the present invention to provide a knee joint structure of an artificial limb having excellent stability when an ankle is landed, being capable of absorbing shock during ankle landing and smooth knee bending during toe take-off, and capable of improving appearance during walking, by employing a pure link mechanism with its simple mechanism, which a physically handicapped person with wide range of muscle power can use without requiring special training.

Actuation

When thus formed, in the idle leg phase shown in FIG. 3, an auxiliary front link 3 and a lower link 4 are widened to be pressed by means of an elastic element 8, and is pressed against a second stopper 7. The auxiliary front link 3 and lower link 4 operate integrally. Thus, a link mechanism operates as if it were a four-joint link. A knee can swing universally when a first cross point P10 is defined as a virtual rotation center axis. The knee stretch position is restricted by a first stopper 6. When the knee is bent, the virtual rotation center axis moves along a single dotted line from the first cross point P10. When the knee is bent, and the knee joint is bent as one sits on the floor with one's knee being bent, the link mechanism is deformed as indicated by a double dotted line. Then, the virtual rotation center axis moves along the single dotted line to the cross point P11. The above actuation is identical to that of a conventional four-joint link knee joint structure.

Now, actuation at a moment when the ankle of the foot part 11 is landed on the ground level GL after the idle leg phase has moved to the leg grounding phase will be described with reference to FIG. 4. When the angle is landed on the ground level GL, and a weight is applied, the line of action of such load is obtained as the line of action F1 or F2 according to whether the stretched muscle of the thigh joint of the physically handicapped person wearing the artificial limb is strong or weak. Here, the lines of action F1 and F2 both pass through the rear of a second cross point P20. Thus, a force is applied to the lower link 4, such that an angle formed by the auxiliary front link 3 and lower link 4 is reduced against the elasticity of the elastic element 8, and the elastic element 8 is compressed. Then, the angle formed by the auxiliary front link 3 and lower link 4 is reduced, and the auxiliary front link 3 leaves the second stopper 7. As a result, an interval between axes 22 and 24 is reduced, and an angle formed by a main front link 2 and a rear link 5 is reduced as compared with a case of the idle leg phase shown in FIG. 3. Thus, the virtual rotation center axis of the knee joint that is a cross point between an extension line of the main frontal link 2 and that of the rear link 5 moves from the cross point P10 shown in FIG. 3 to a cross point P12 shown in FIG. 4.

As shown in FIG. 4, the virtual rotation center axis moves to the cross point P12 far upward and rear of the link mechanism. Thus, irrespective of whether the stretched muscle of the thigh joint of the physically handicapped person is string or weak, the lines of action F1 and F2 pass through the far front of the cross point P12 that is the virtual rotation center axis, and thus, a knee is not bent during angle landing. That is, a physically handicapped person with one's strong or weak muscle power can do stable landing free of knee bending during ankle landing when the idle leg phase goes to the leg grounding phase. Further, during ankle landing, the elastic element 8 is compressed, and thus, acts as a shock absorber. Thus, this element can mitigates shock applied to the physically handicapped person during ankle landing. Furthermore, the knee is slightly bent around the axis 23 during ankle landing, and thus, a movement similar to that during ankle landing of a healthy person is achieved, improving the appearance during walking.

When walking is advanced in the leg grounding phase from the state of ankle landing, the line of action due to the weight's load moves from the ankle of the foot part 11 toward the toe. FIG. 5 is a diagram illustrating an actuation of a link mechanism in the middle of such movement. At the line of action F3 due to a load, a start point advances to the vicinity of the center of the foot part 11, passes through the rear vicinity of the second cross point P20, and extends upwardly. Since the line of action F3 passes through the vicinity of the second cross point P20, a force component of compressing the elastic element 8 decreases from among the divisional forces of the forces along the line of action F3. Thus, the elastic element 8 slightly extends, and an angle between the auxiliary front link 3 and the lower link 4 is slightly increased. However, the second stopper 7 does not abut against the auxiliary front link 3. Therefore, an interval between the axes 22 and 24 is slightly increased, and the virtual rotation center axis of the knee joint moves to a cross point P13 between the extension line of the main front link 2 and that of the rear link 5. That is, the virtual rotation center axis that moved from a position of the cross point P10 shown in FIG. 3 to the cross point P12 shown in FIG. 4 due to ankle landing gradually returns toward the position of the cross point P10 in accordance with advancement of walking.

When walking is further advanced so that the line of action F3 of a load is forward of the second cross point P20, a force component of compressing the elastic element 8 is eliminated from among the divisional forces of the forces along the line of action F3. Thus, the elastic element 8 extends, and an angle between the auxiliary front link 3 and the lower link 4 is fully increased. Then, the second stopper 7 abuts against the auxiliary front link 3 so as to inhibit the angle between both of these links 3 and 4 from being increased. When the line of action F3 of a load is forward of the second cross point P20, the divisional force of the forces along the line of action F3 acts to open both of the links 3 and 4. Therefore, the second cross point P20 can be considered as a "key virtual center axis" for identifying whether the load from the foot part 11 is derived from the ankle or toe. When the line of action F3 of a load is rearward of the second cross point P20 that is a "key virtual center axis", it is identified that the load is derived from the ankle. Then, the elastic element 8 is compressed, and the virtual rotation center axis of the knee joint is positioned close to the cross point P12 that is far upward and rearward of the link. On the other hand, when the line of action F3 of a load is forward of the second cross point P20 that is a "key virtual center axis", it is identified that the load is derived from the toe. Then, the second stopper 7 works, and the virtual rotation center axis of the knee joint is obtained as a first cross point P10 close to the link.

FIG. 6 is a diagram illustrating an actuation of a link mechanism during toe load. The line of action F5 of a load in the case where the bent muscle of the thigh joint of the physically handicapped person wearing an artificial limb is strong and the line of action F6 of a load in the case where the bent muscle is weak are forward of the second cross point P20 that is a "key virtual center axis" as well. Thus, it is identified that the load is derived from the toe, and an angle between the auxiliary frontal link 3 and the lower link 4 is increased. Then, the second stopper 7 works, and the virtual rotation center axis of the knee joint is obtained as a first cross point P10 close to the link. Then, both of the lines of action F5 and F6 pass through the rear of the first cross point P10 that is a virtual rotation center axis. Thus, knee bending is started around the first cross point P10, and smooth toe take-off takes place.

Namely, according to a construction of the present invention, the length of each of the links 1 to 5 is properly designed, whereby the virtual rotation center axis of the knee joint during an ankle load, i.e., a cross point P12 can be set at a sufficiently high and rear position. Thus, stable ankle landing free of knee bending can be done irrespective of whether the muscle power of a physically handicapped person wearing an artificial limb is strong or weak, and migration from the idle leg phase to the leg grounding phase can be done constantly. In addition, the virtual rotation center axis of the knee joint during toe load, i.e., the first cross point P10 can be set close to a link mechanism. Thus, the lines of action F5 and F6 of a load during toe load can pass through the rear of the first cross point P10, and knee bending during such toe load can be done smoothly irrespective of whether the muscle power is strong or weak. Migration from the leg grounding phase to the idle leg phase is smoothened. Moreover, a key axis for identifying between the ankle load and the toe load is defined as a second cross point P20 that is a virtual center axis positioned beneath the link mechanism. Thus, the position of the second cross point P20 is properly set, whereby identification between the ankle load and the toe load can be accurately done irrespective of whether the muscle power is strong or weak. Therefore, one knee joint structure can be used by a physically handicapped person with a wide range of muscle power without requiring special training.

As has been described above, the present invention has the following advantage.

(1) A pure link mechanism with its simple mechanism is employed, thus ensure high cost efficiency and durability.

(2) Excellent stability when an ankle is landed is achieved.

(3) The shock during ankle landing is absorbed by an elastic element, the shock applied to a physically handicapped person is reduced, and usability is high.

(4) A knee is smoothly bent during toe take-off, and migration from the leg grounding phase to the idle leg phase is smooth.

(5) The appearance during walking is good.

(6) A physically handicapped person with a wide range of muscle power can use it without requiring special training.

DETAILED DESCRIPTION OF THE PREFERRED EMBODIMENTS

Figure 7:
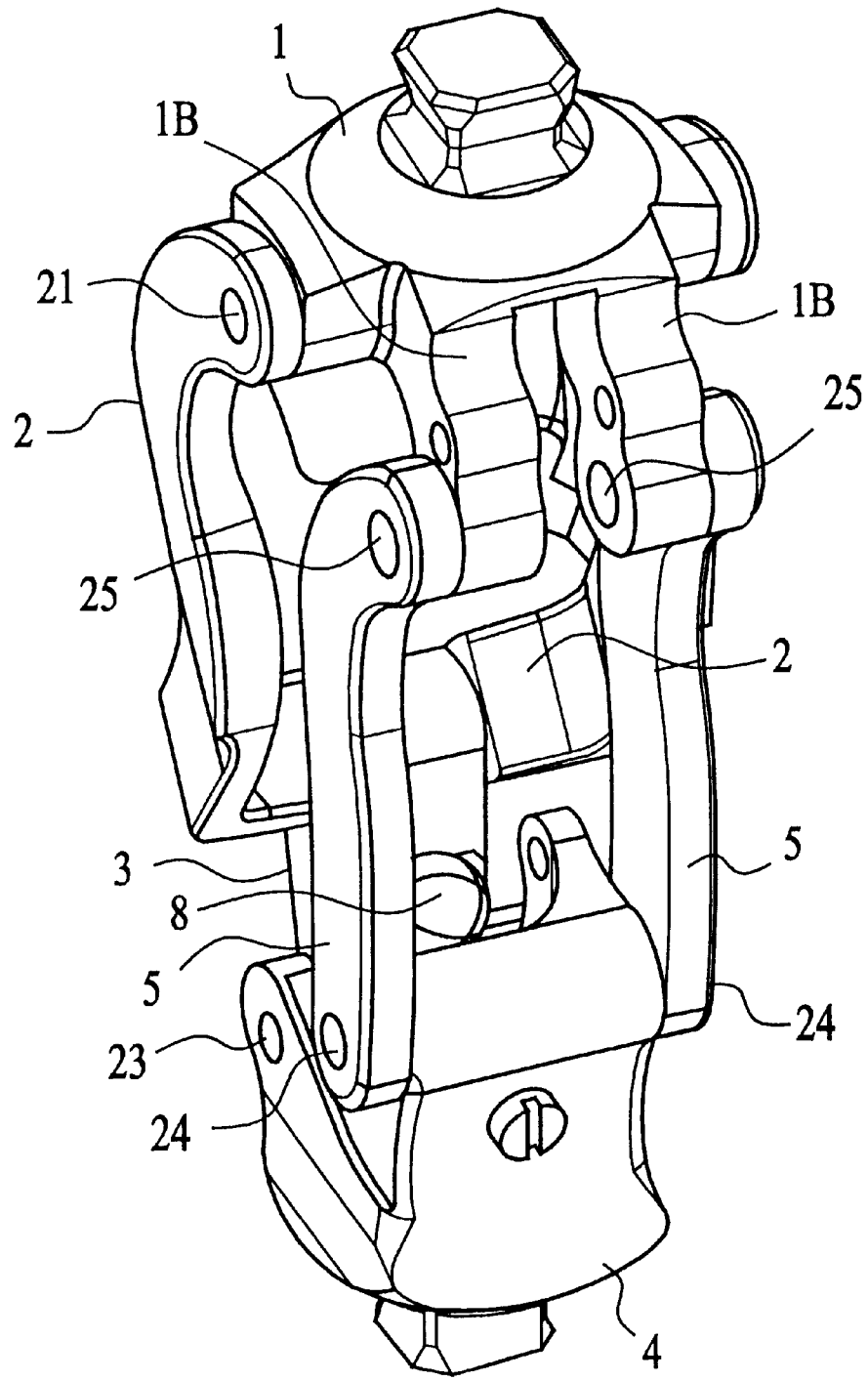
FIG. 7 is a perspective view showing a knee joint structure viewed from a diagonally rear according to an embodiment.
Figure 8:
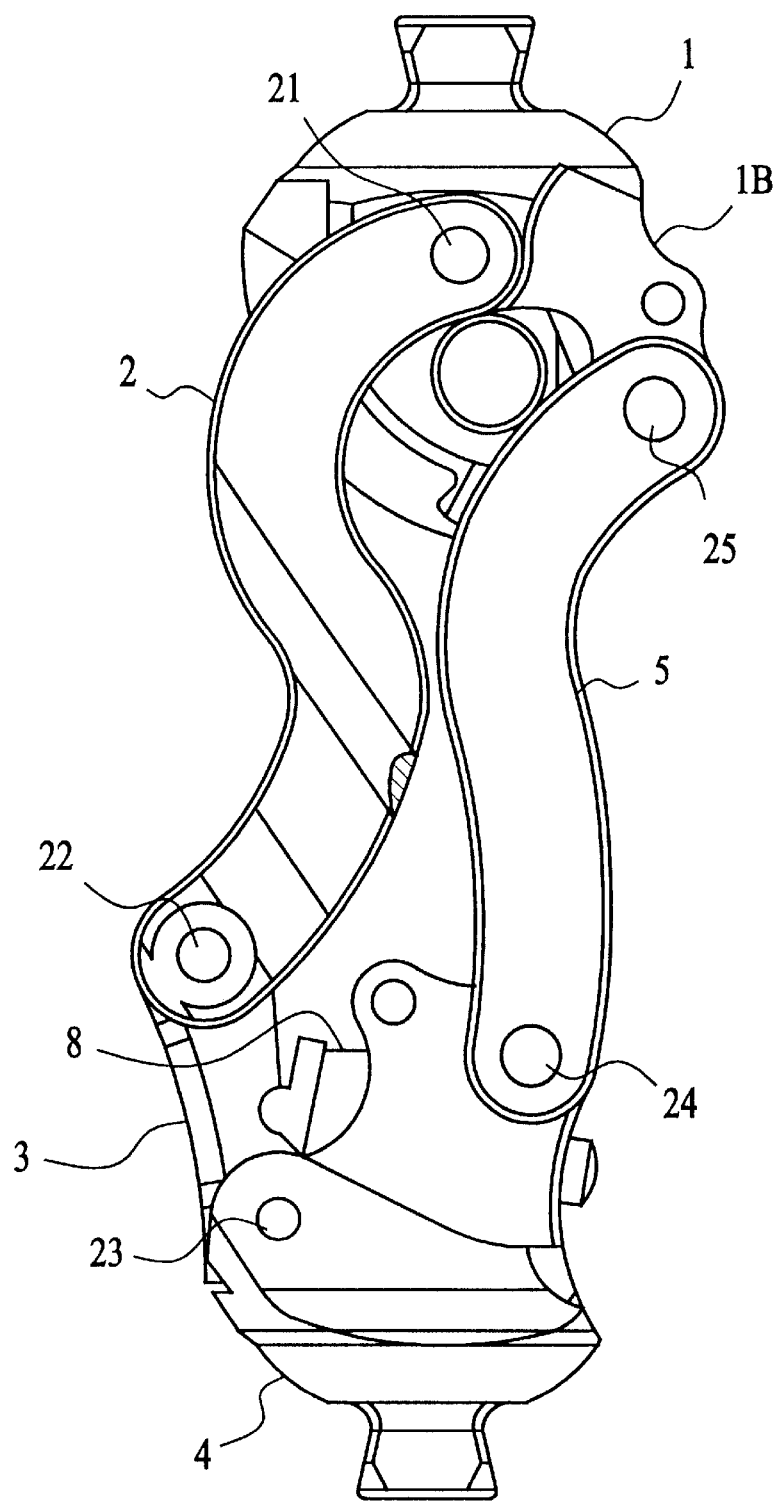
FIG. 8 is a side view showing a knee joint structure.

FIG. 7 is a perspective view showing a knee joint structure according to the present invention, and FIG. 8 is a side view showing the knee joint structure. In these figures, a damper 31 for linking the upper link 1 and the lower link 4 with each other described later is not shown. FIG. 7 is a slightly rear-view of the structure. At the right and left of the-upper link 1 that comprises a substantially disk shaped block-like member, main frontal links 2, 2 comprising of two plate shaped members curved in a substantially S shape are rotatably linked with each other by means of a shaft 21. An auxiliary frontal link 3 comprising one plate shaped block is arranged downward of the main frontal links 2, 2, and the main frontal link 2, 2 and the auxiliary frontal link 3 are rotatably linked with each other by means of the shaft 22. The auxiliary frontal link 3 is linked with the substantially disk block shaped lower link 4 by means of a shaft 23. The rear between the lower link 4 and the upper link 1 is linked by means of rear links 5, 5 comprising two plate shaped members curved in a substantially V shape. That is, the lower parts of the rear links 5, 5 are linked with the lower link 4 by means of a shaft 24. The upper parts of the rear links 5, 5 are linked by means of shafts 25, 25 to arm portions 1B, 1B extending rearward of the upper link 1. As shown in FIG. 8, a five-joint link mechanism is configured by the shafts 21, 22, 23, 24, and 25. An elastic element 8 made of a cylindrical rubber is inserted to be sandwiched between the auxiliary frontal link 3 and the lower link 4, and is biased so as to increase an angle formed by the auxiliary frontal link 3 and the lower link 4.

Figure 1:
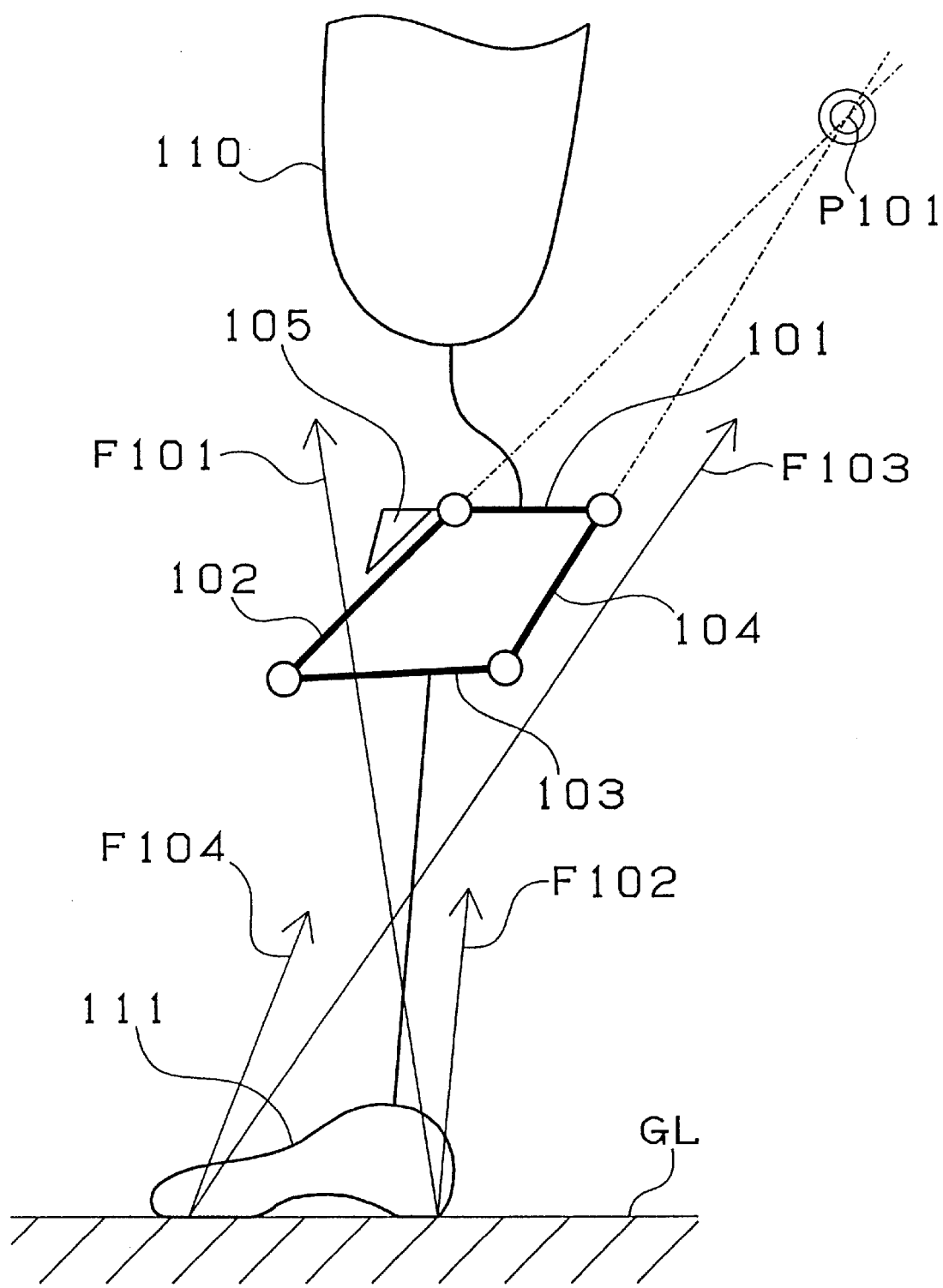
FIG. 1 is a diagram showing a conventional knee joint employing a four-joint link mechanism.
Figure 2:
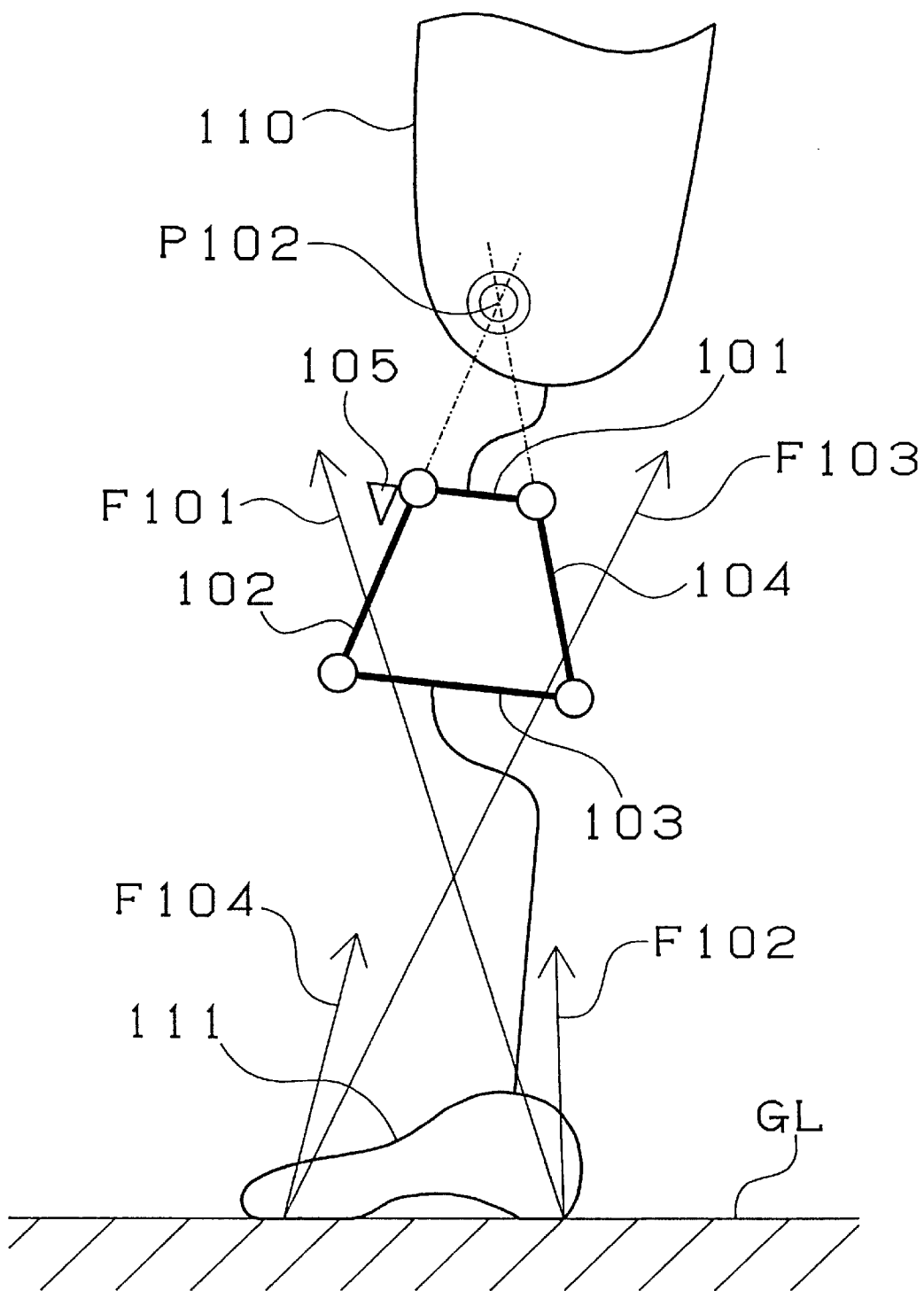
FIG. 2 is a diagram showing another conventional knew joint employing a four-joint link mechanism.
Figure 3:
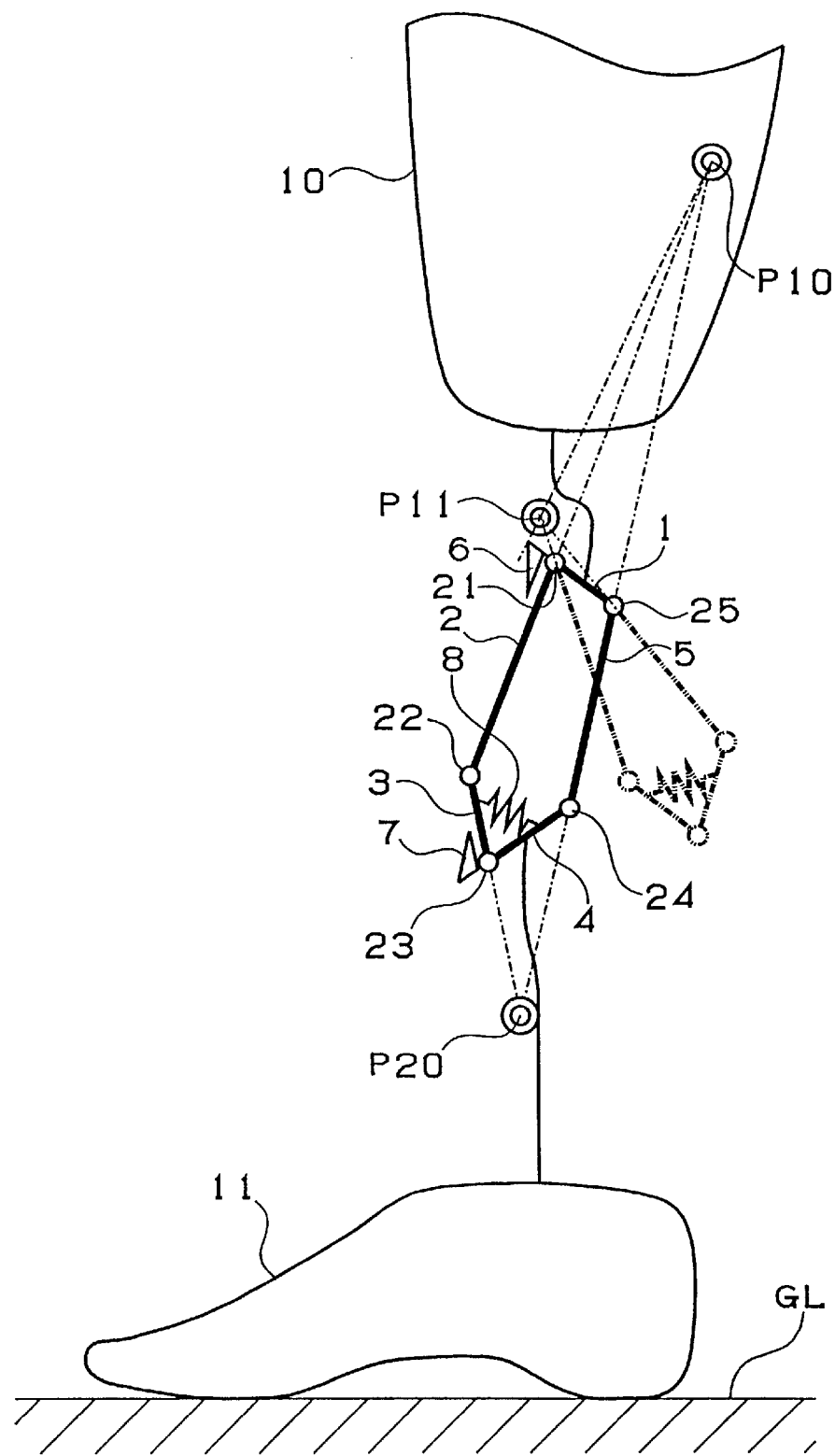
FIG. 3 is a diagram showing a knee joint employing a five-joint link mechanism according to the present invention, the figure showing a case of an idle leg phase.
Figure 4:
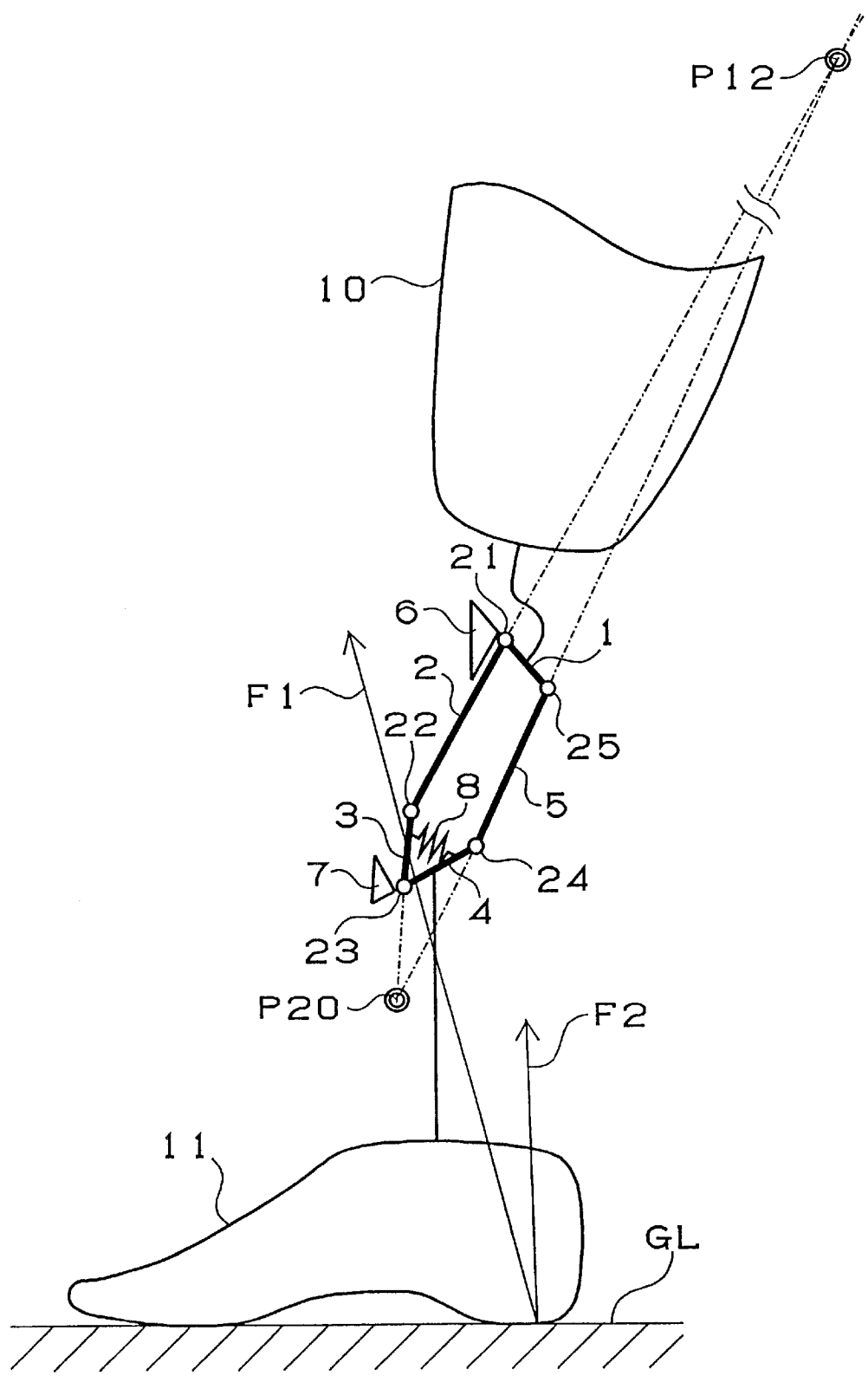
FIG. 4 is a diagram showing a knee joint employing a five-joint link mechanism during ankle landing.
Figure 5:
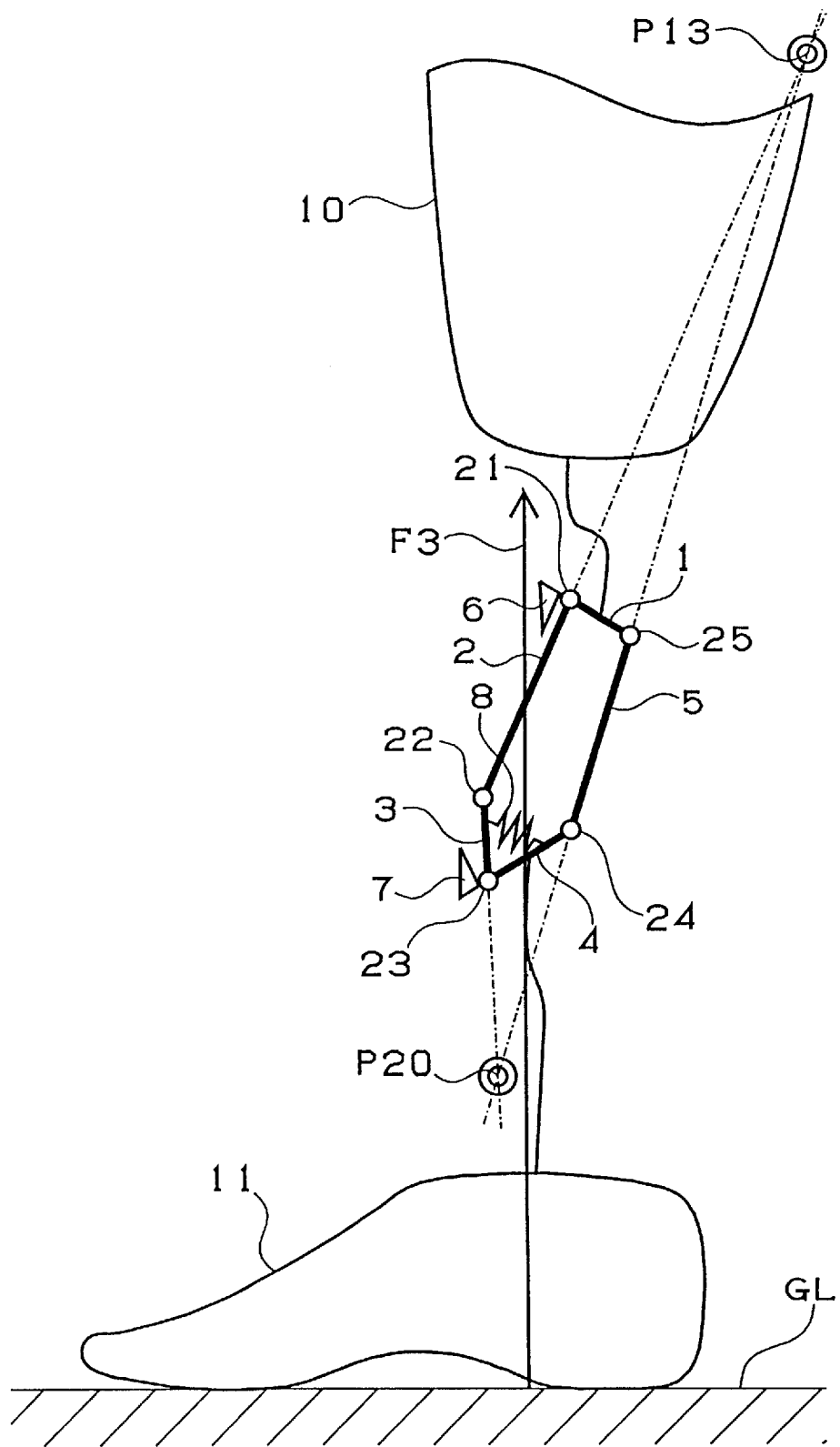
FIG. 5 is a diagram showing a knee joint employing a five-joint link mechanism in the middle of a leg grounding phase.
Figure 6:
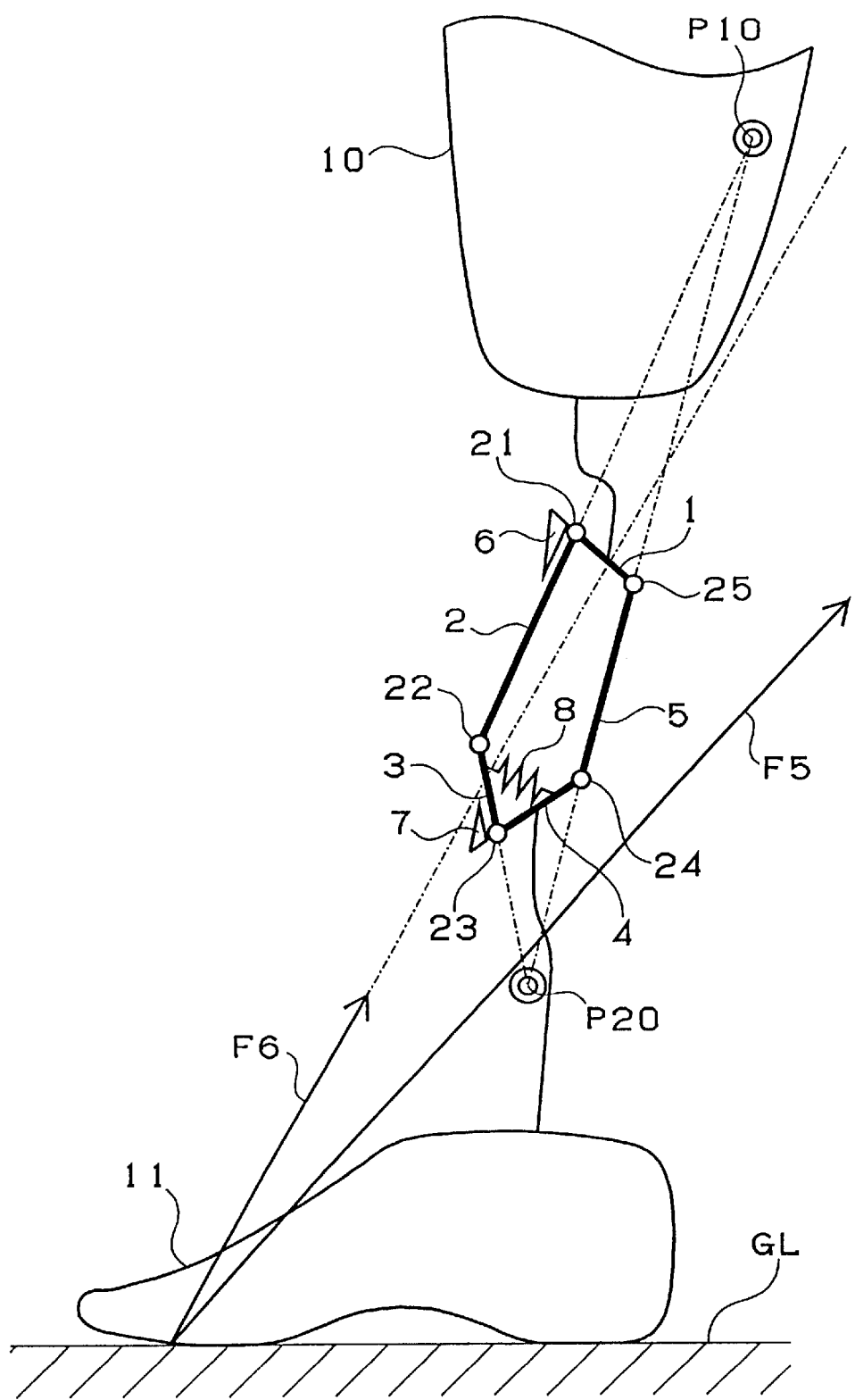
FIG. 6 is a diagram showing a knee joint employing a five-joint link mechanism during toe take-off.
Figure 9:
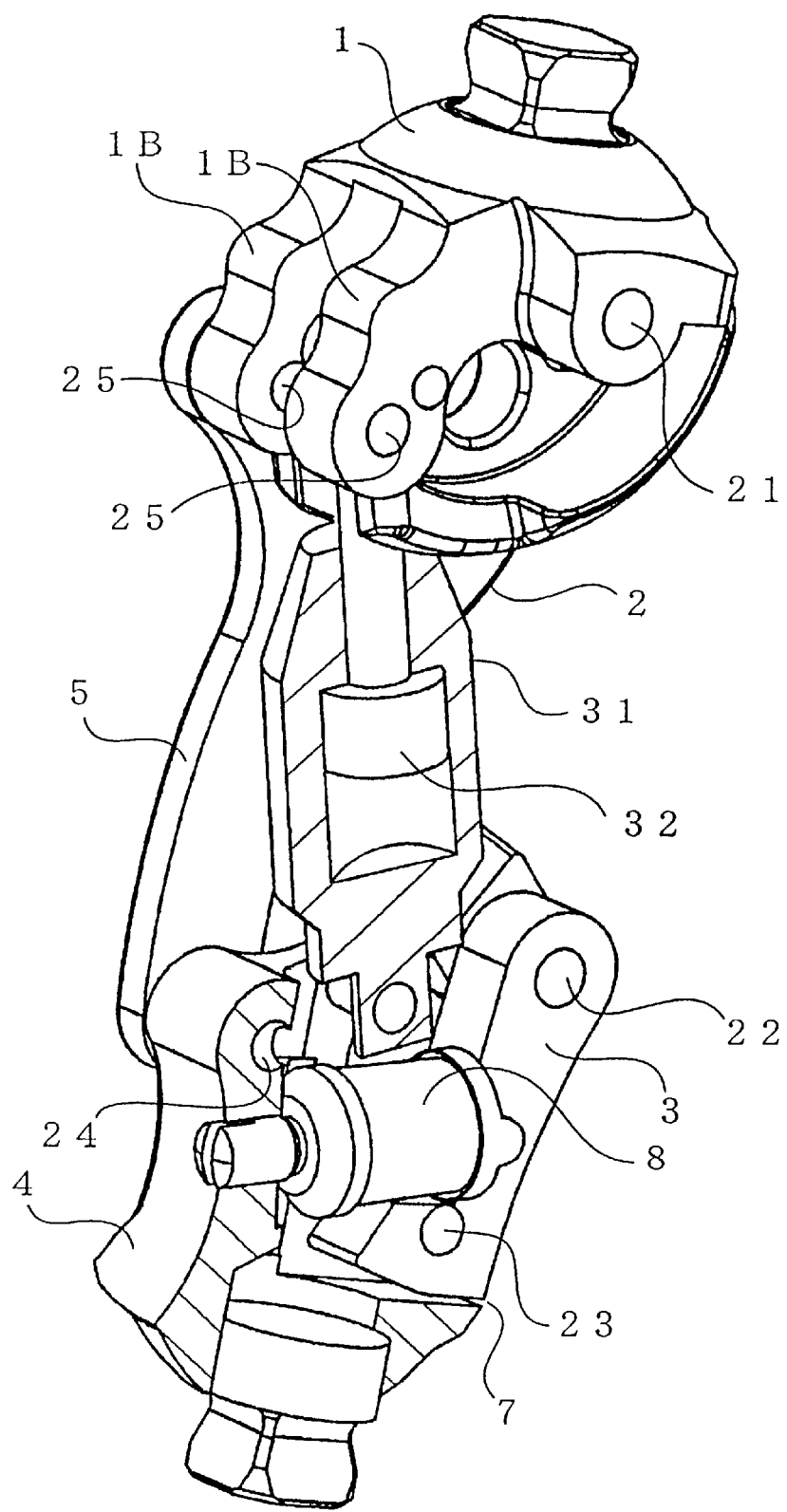
FIG. 9 is a perspective view showing a knee joint structure in an idle leg phase.
Figure 10:
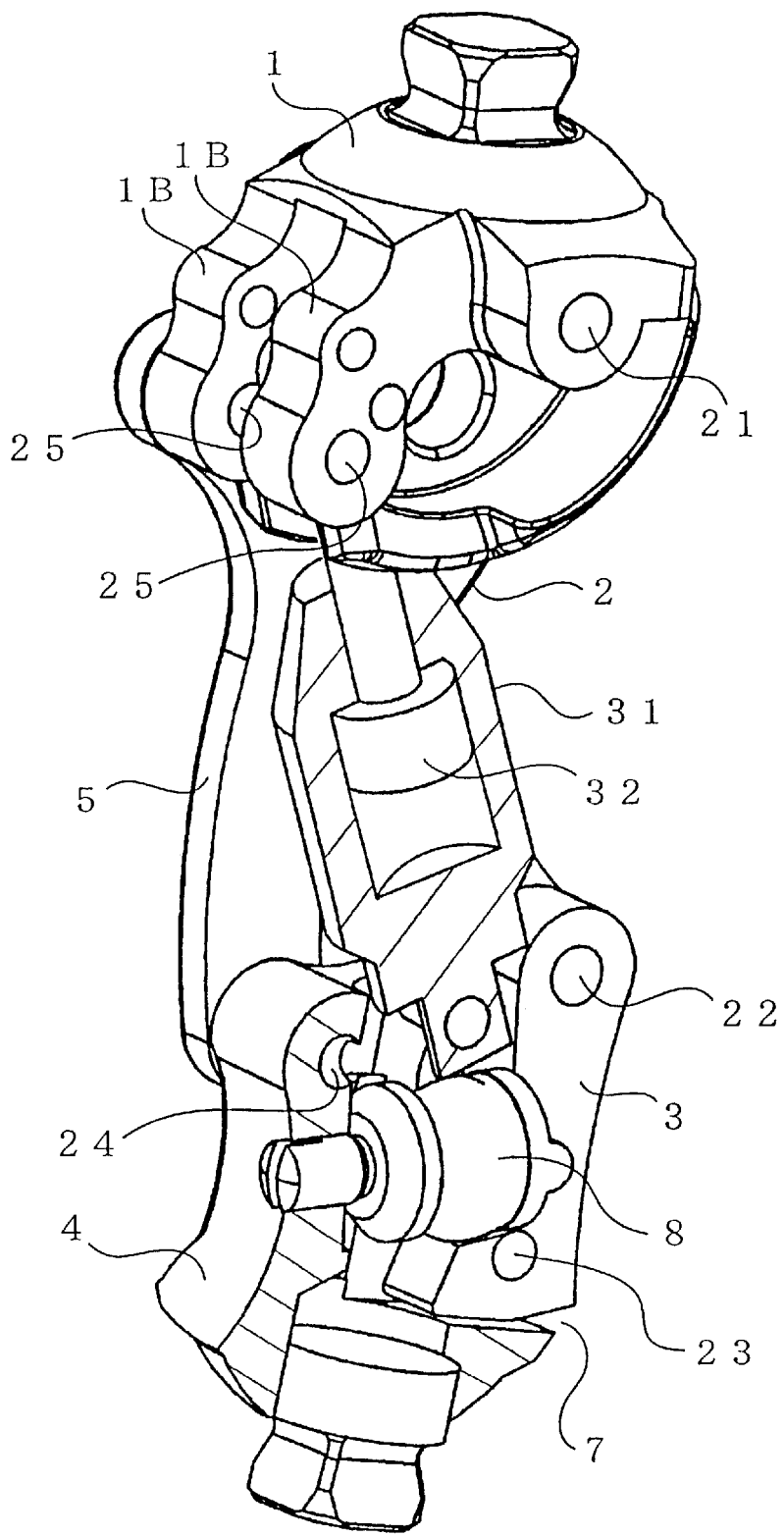
FIG. 10 is a perspective view showing a knee joint structure during ankle landing.

FIG. 9 and FIG. 10 are perspective views when this knee joint structure is viewed from a diagonal rear, part of which is fragmentarily shown, and where a main frontal link 2 at the right side and a rear link 5 at the right side are not shown. In these figures, a damper 31 is added. The damper 31 is linked between the upper link 1 and the lower link 4, and acts to restrain actuation during knee bending from being abnormally accelerated due to action of a damper piston 32. FIG. 9 shows a knee joint structure established in the state of FIG. 3 that is in an idle leg phase. In this state, the cylindrical rubber based elastic element 8 extends, and one lower side of the auxiliary frontal link 3 abuts against one upper side of the lower link 4 so as to prevent an angle between the auxiliary frontal link 3 and the lower link 4 from being further increased. One lower side of the auxiliary frontal link 3 and one upper side of the lower link 4 constitute a second stopper 7. FIG. 10 shows a knee joint structure in the state of FIG. 4 that is during ankle landing. In this state, the cylindrical rubber based elastic element 8 is crushed, and an angle formed by the auxiliary frontal link 3 and the lower link 4 is slightly decreased. One lower side of the auxiliary frontal link 3 and one upper side of the lower link 4 are opened while the second stopper 7 does not act.

Figure 11:
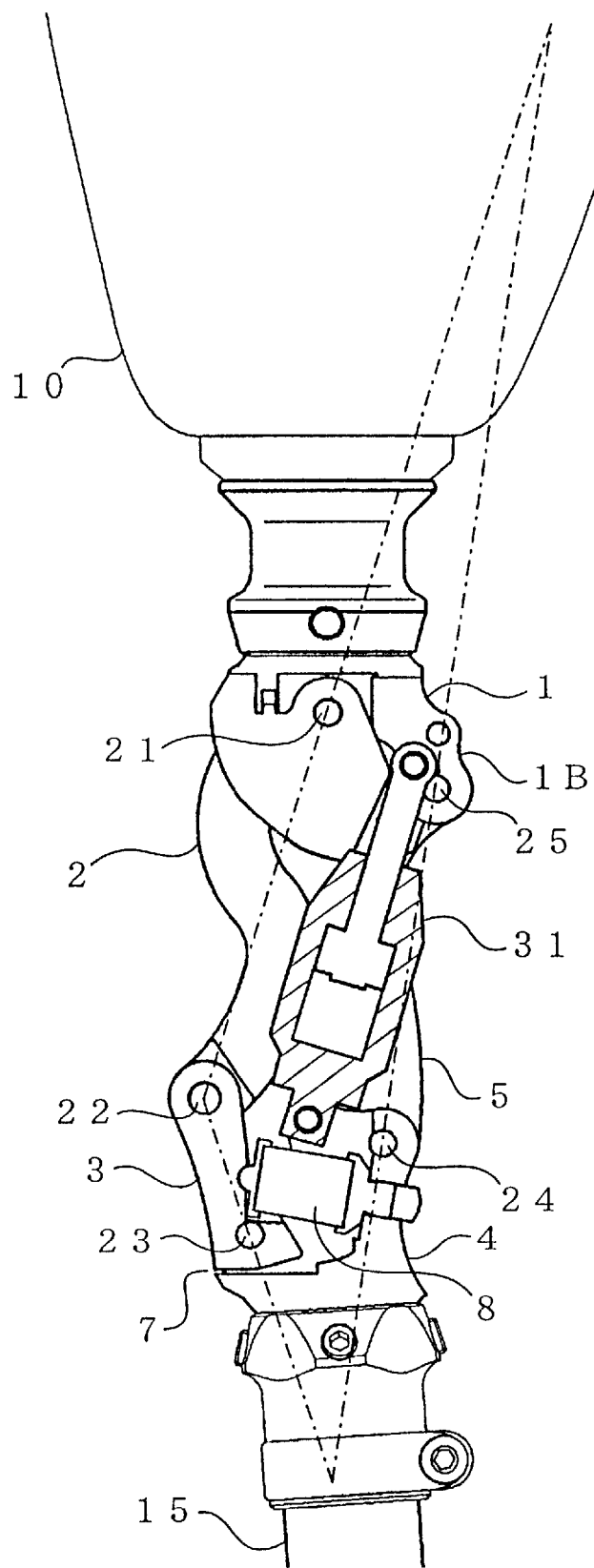
FIG. 11 is a side view showing a knee joint structure when a thigh support part is mounted in an idle leg phase.
Figure 12:
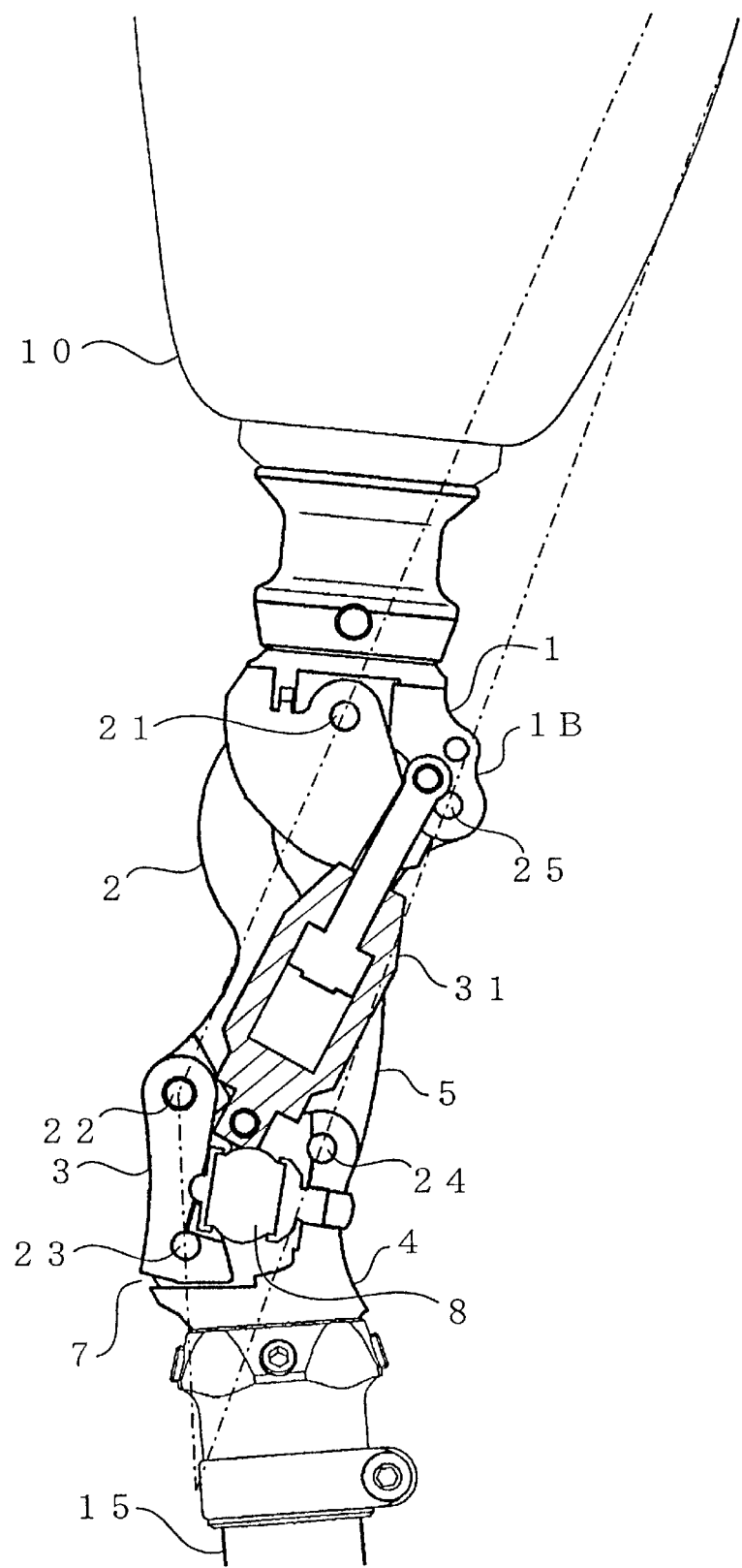
FIG. 12 is a side view showing a knee joint structure when a thigh support part is mounted during ankle landing.

FIG. 11 and FIG. 12 are side views each showing a state in which a thigh support part 10 and a foot part 11 (not shown) are mounted on this knee joint structure, part of which is fragmentarily shown, where a main frontal link 2 at the left side and a rear link 5 at the left side are not shown. The thigh support part 10 is fixed to the upper link 1. A pipe 15 corresponding to a skeleton of shin is fixed to the lower link 4. The foot part 11 (not shown) is linked with a tip end of the pipe 15. FIG. 11 shows a knee joint structure established in the state of FIG. 3 that is in an idle leg phase. In this state, a cylindrical rubber based elastic element 8 extends, and a cross point between extension lines of the main frontal link 2 and the rear link 5 indicated by a single dotted line is positioned comparatively close to a link mechanism. FIG. 12 shows a knee joint structure established in the state of FIG. 4 that is during ankle landing. In this state, the cylindrical rubber based elastic element 8 is crushed, and a cross point between the extension lines of the main frontal link 2 and the rear link 5 indicated by a single dotted line is positioned at a far rear and high position of the link mechanism.

Figure 13:
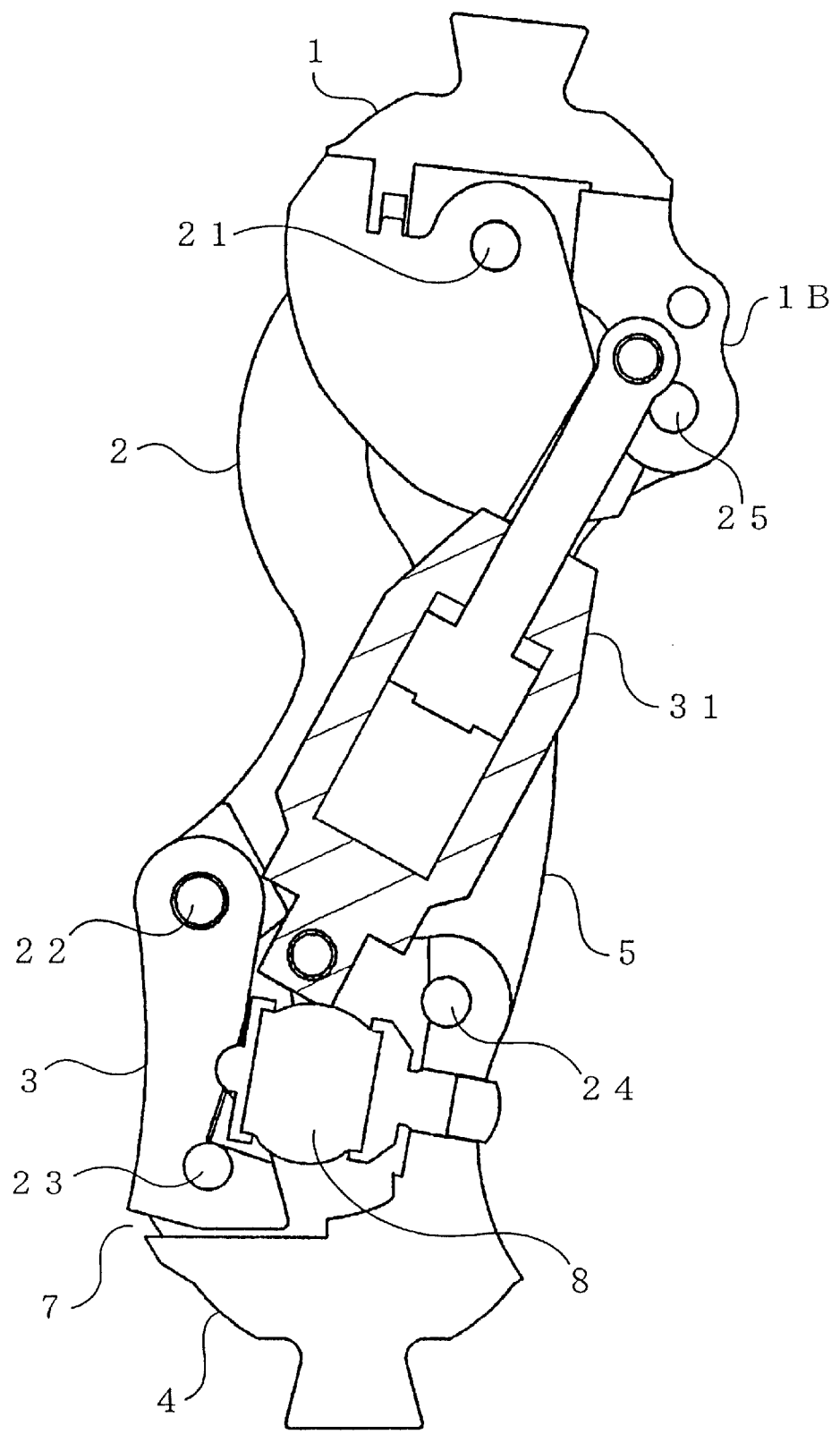
FIG. 13 is a side view showing a knee joint structure during ankle landing.
Figure 14:
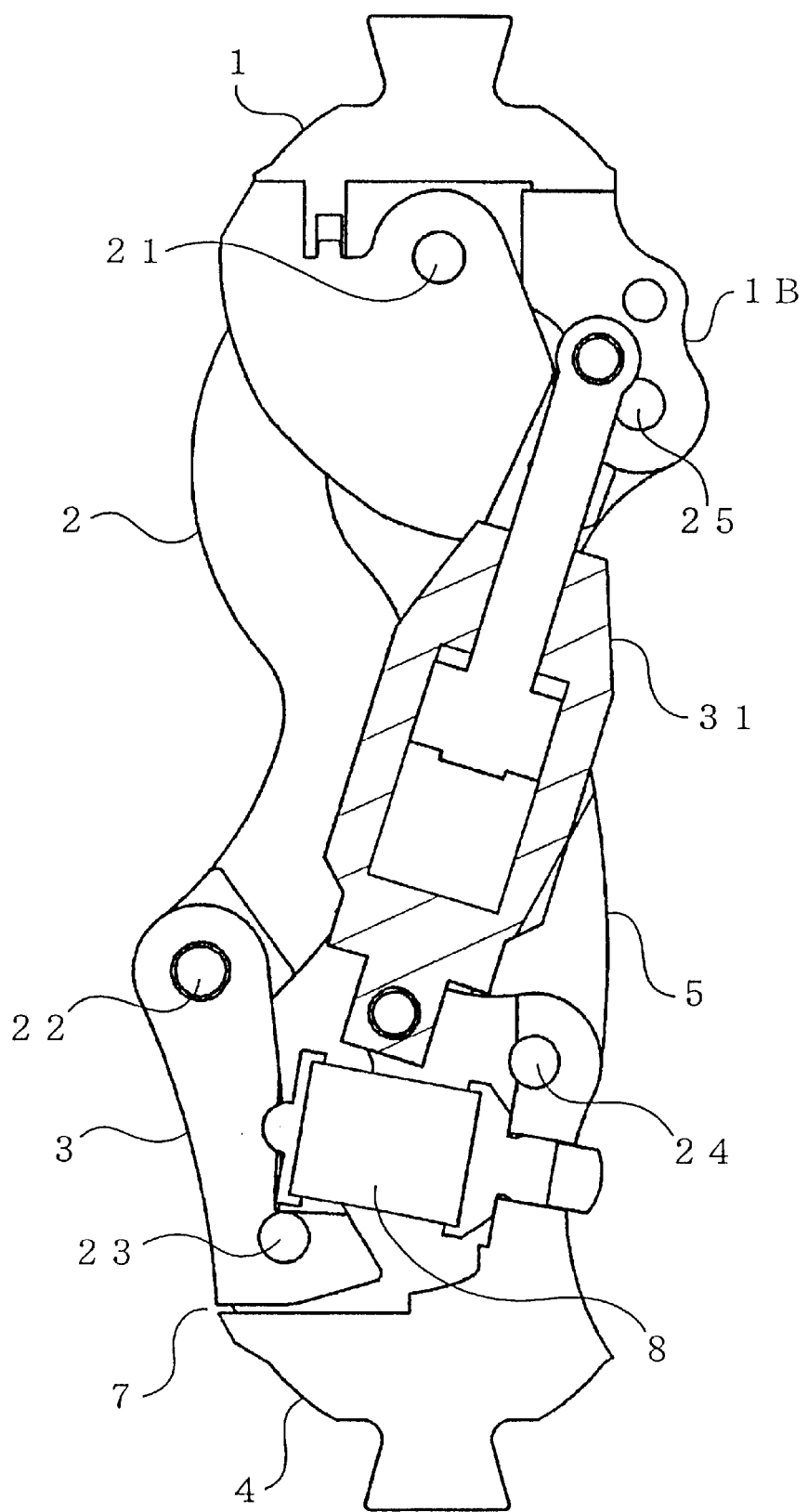
FIG. 14 is a side view showing a knee joint structure in a state in which a knee is extended in an idle leg phase.
Figure 15:
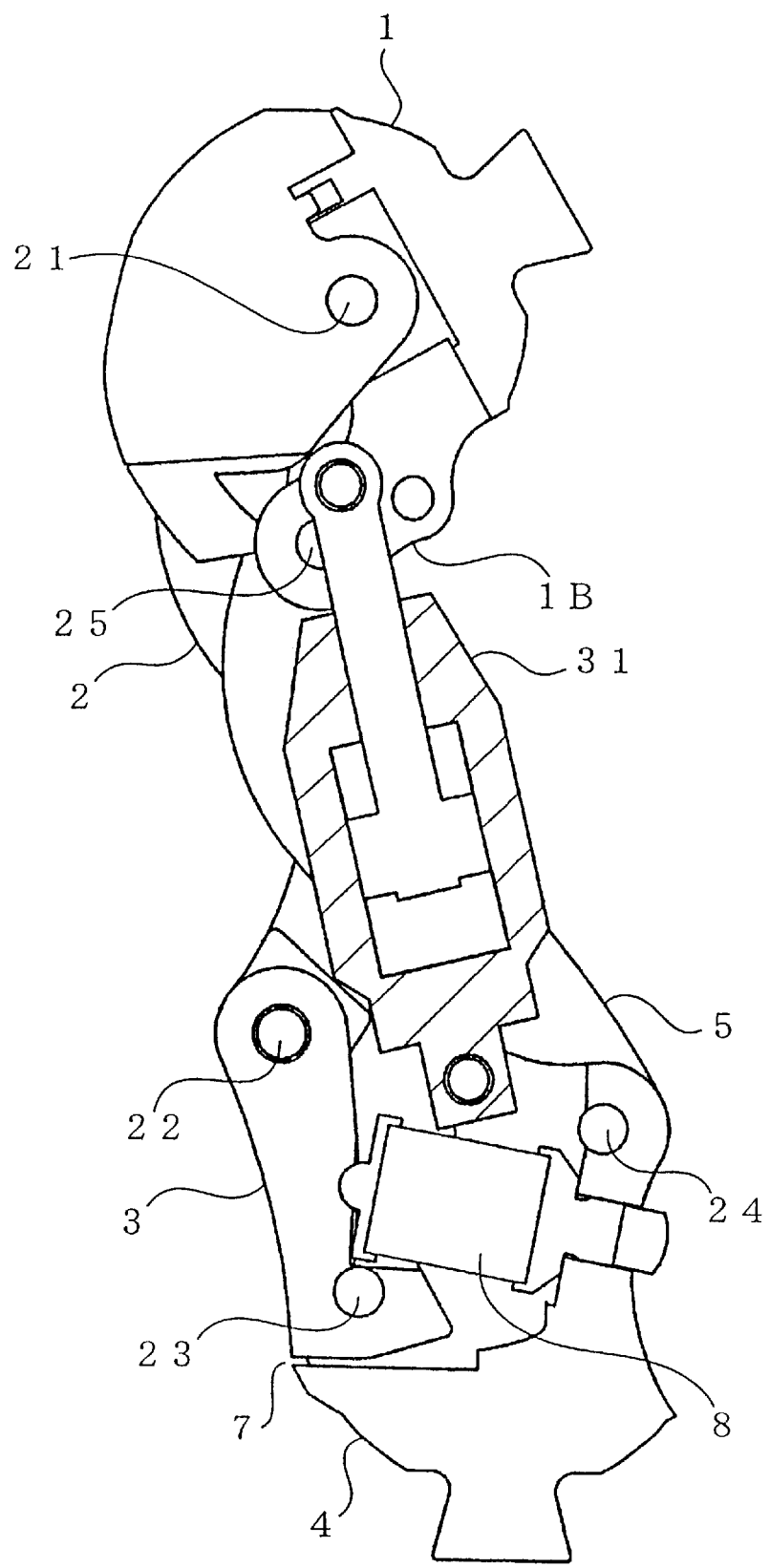
FIG. 15 is a side view showing a knee joint structure when a knee is bent at about 60 degrees in an idle leg phase.
Figure 16:
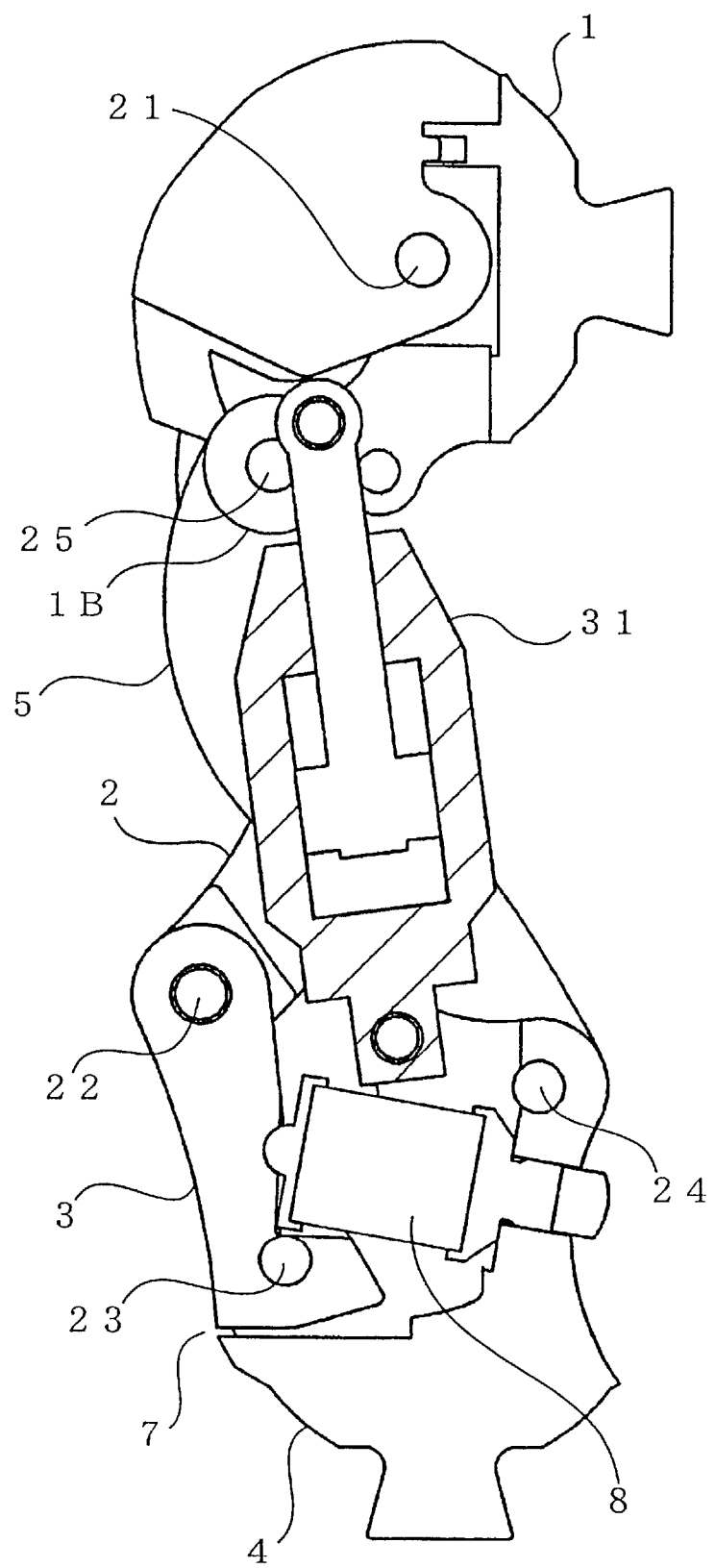
FIG. 16 is a side view showing a knee joint structure when a knee is bent at about 90 degrees in an idle leg phase.
Figure 17:
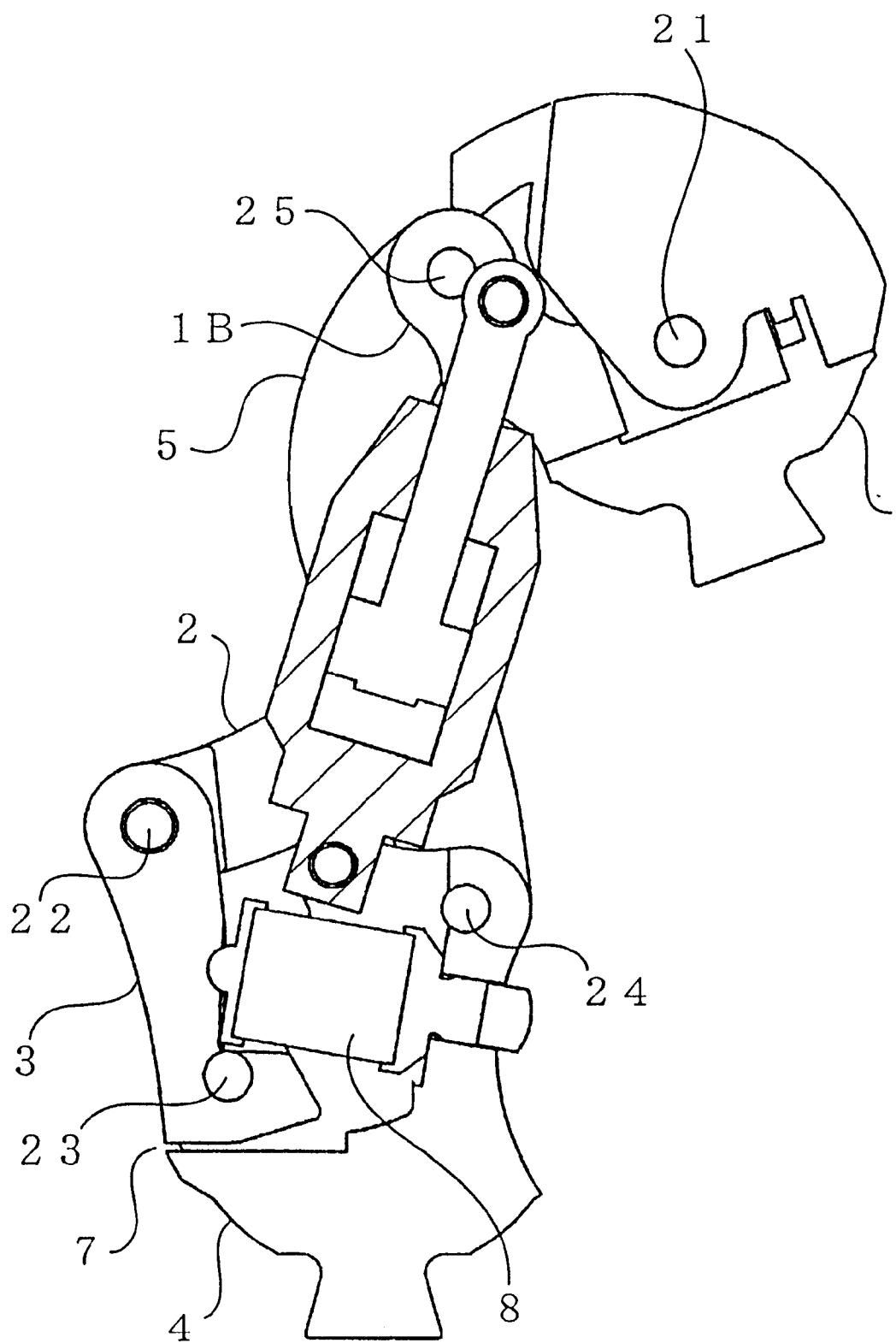
FIG. 17 is a side view showing a knee joint structure when a knee is bent at about 160 degrees in an idle leg phase.

FIG. 13 to FIG. 17 are side views showing how is a knee joint structure at various postures, part of which is fragmentarily shown, and part of which is not shown. FIG. 13 shows a knee joint structure in a state in which a ankle is landed. FIG. 14 shows a knee joint structure in a state in which a knee extends in an idle leg phase. FIG. 15 shows a state in which the knee is bent at about 60 degrees in the idle leg phase. FIG. 16 shows a state in which the knee is bent at about 90 degrees in the idle leg phase. FIG. 17 shows a state in which the knee is bent at about 160 degrees in the idle leg phase as if one sits on the floor with one's knee being bent. In this way, when the knee is bent, a virtual rotation center axis that is determined depending on a cross point between a straight line connecting the axes 21 and 22 with each other and a straight line connecting the axes 24 and 25 with each other is brought into the proximity or inside of the link mechanism, whereby the center line can be folded to be small.

Figure 18:
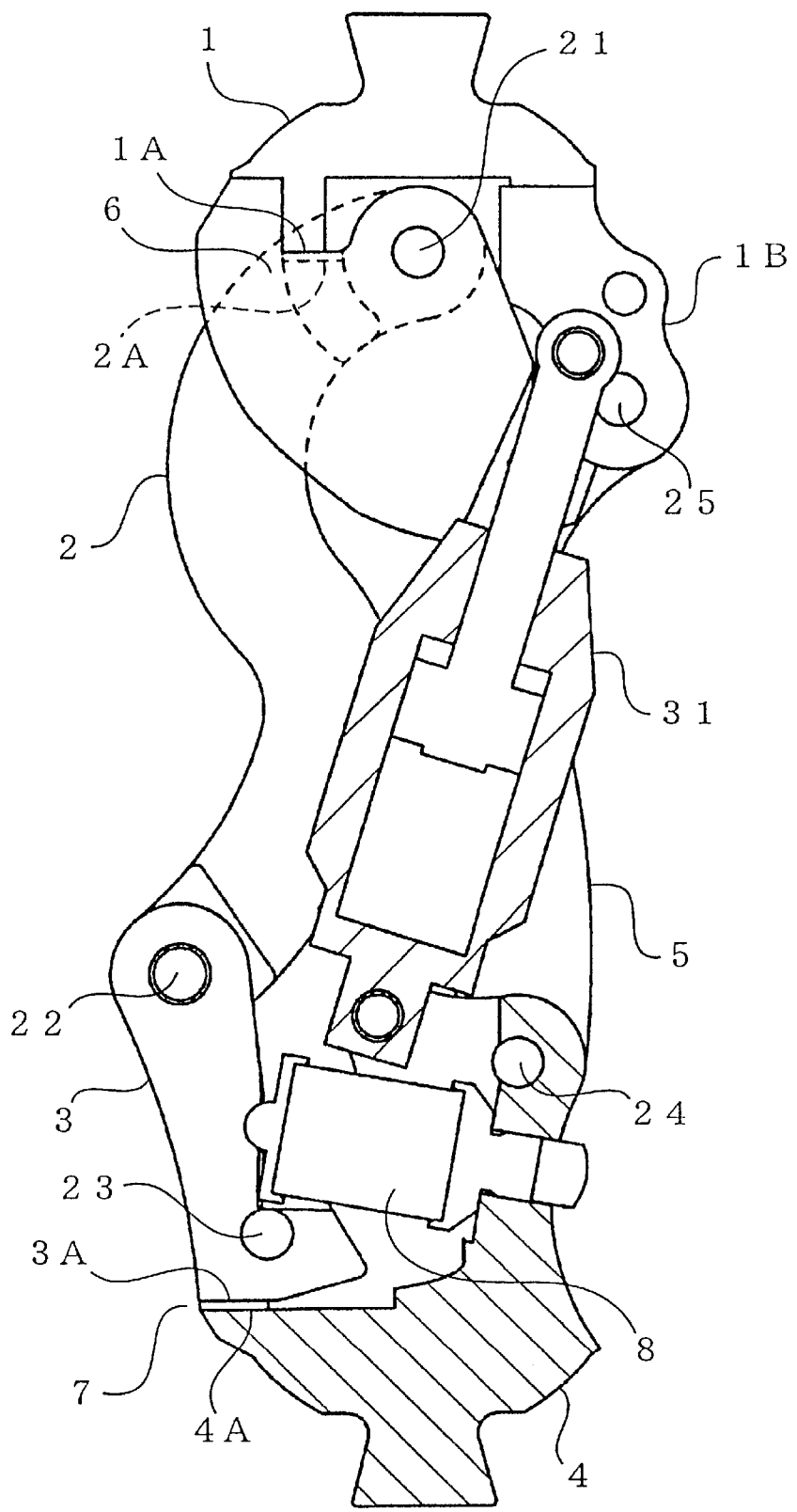
FIG. 18 is a side view showing a knee joint structure illustrating a structure of a first stopper and a second stopper.

FIG. 18 is a side view of a knee joint structure illustrating a structure of a first stopper 6 inhibiting forward expansion of a main frontal link 2 and a second stopper 7 inhibiting forward expansion of the auxiliary frontal link 3. The first stopper 6 is composed of a protrusive face 1A of the upper link 1 and a face 2A indicated by an upward dashed line of the main frontal link 2. When the main frontal link 2 rotates in the clockwise direction of the figure, namely, in a direction in which the knee is extended forward with the axis 21 being a rotation center, a face 2A of the main frontal link 2 is inhibited in abutment against a face 1A of the upper link 1. The first stopper 6 is provided to inhibit an angle formed by the upper link 1 and the main frontal link 2 from being increased to a predetermined angle or more. The second stopper 7 is composed of a face 3A of a lower side of the auxiliary frontal link 3 and a face 4A of an upper side of the lower link 4. When the auxiliary frontal link 3 rotates in the counter-clockwise direction of the figure, namely, in a direction in which the auxiliary frontal link 3 is extended forward with the axis 23 being a rotation center, a face 3A of the auxiliary frontal link 3 is inhibited in abutment against a face 4A of the lower link 4. The second stopper 7 is provided to inhibit an angle formed by the auxiliary frontal link 3 and the lower link 4 from being increased to a predetermined angle or more.

Although the invention has been disclosed in the context of a certain preferred embodiments, it will be understood that the present invention extends beyond the specifically disclosed embodiments to other alternative embodiments of the invention. Thus, it is intended that the scope of the invention should not be limited by the disclosed embodiments but should be determined by reference to the claims that follow.

What is claimed is:

1. A knee joint structure of an artificial limb having a five-joint link mechanism, including five-joint links that consists of an upper link to which a thigh support part of an artificial limb is fixed; a lower link with which a foot part of the artificial limb is connected; a rear link connecting the upper link and the lower link with each other; a main frontal link linked with a front of the upper link, and an auxiliary frontal link connecting the main frontal link and the lower link with each other, said structure comprising:

a first stopper for inhibiting an angle formed by said upper link and main frontal link from being increased to a predetermined angle or more;

a second stopper for inhibiting an angle formed by the auxiliary frontal link and the lower link from being increased to a predetermined angle or more; and an elastic element inserted to be sandwiched between the auxiliary frontal link and the lower link, the elastic element acting to increase an angle formed by both of the links, wherein a length of said each link is set in such a manner that a cross point between an extension line of said main frontal link and that of a rear link is positioned upward of said each link, and a cross point between an extension line of said auxiliary frontal link and that of the rear link is positioned downward of said each link.

2. A knee joint structure of an artificial limb as claimed in claim 1, wherein the length of each link and the position and inclination relevant to a foot part are set so that a position of a cross point between an extension line of said main frontal link and that of the rear link (hereinafter, referred to a first cross point) is positioned upward and rear of five links and any of the five joints connecting each of the five links and rear of an ankle of a foot part in a state in which a knee is extended, and the first stopper abuts.

3. A knee joint structure of an artificial limb as claimed in claim 1, wherein the length of each link and the position and inclination relevant to a foot part are set so that a position of a cross point between an extension line of said auxiliary frontal link and that of the rear link (hereinafter, referred to a second cross point) is positioned downward of five links and any of the five joints connecting each of the five links and between an ankle of a foot part and a toe in a state in which a knee is extended, and the first stopper abuts.

4. A knee joint structure of an artificial limb as claimed in claim 1, wherein said elastic element consists of a cylindrical rubber based block and is formed so that a length of the rubber based block is such that the rubber based block is established in a substantially free state at an angle position at which an angle formed by the auxiliary frontal link and the lower link is the largest, and the second stopper abuts, and when the angle formed by the auxiliary frontal link and the lower link is reduced, the rubber based block is crushed.

5. A knee joint structure of an artificial limb as claimed in claim 1, wherein said upper link and lower link consist of blocks, the rear link and main frontal link are made of two plate shaped materials, respectively, the auxiliary frontal link is made of a block material whose width is smaller than that of the lower link, and each member is arranged so that the rear link and main frontal link can cross each other when an angle is formed relevant to the upper and lower links (when a knee is bent).

6. A knee joint structure of an artificial limb as claimed in claim 1, wherein a damper for inhibiting approaching and separating speeds of said upper link and lower link is provided between these links.

7. A knee joint structure of an artificial limb as claimed in claim 1, wherein said first stopper is made of a structure in which a part of the upper link and a part of the main frontal link abut against or is released from each other.

8. A knee joint structure as of an artificial limb claimed in claim 1, wherein said second stopper is made of a structure in which a part of the auxiliary frontal link and a part of the lower link abut against or is released from each other.

* * * * *